(12) United States Patent
Liu et al.

(10) Patent No.: US 9,260,534 B2
(45) Date of Patent: Feb. 16, 2016

(54) SITE-DIRECTED PEG-MODIFIED EXENDIN-4 ANALOGS AND USES THEREOF

(75) Inventors: Keliang Liu, Beijing (CN); Yuanjun Liang, Beijing (CN); Xiaoyu Xu, Beijing (CN); Sicheng Li, Chengdu (CN)

(73) Assignees: Institute of Pharmacology and Toxicology Academy of Military Medical Sciences P.L.A. China, Beijing (CN); Chengdu Yiping Medical Science & Technology Co., Ltd., Chengdu, Sichuan (CN)

( * ) Notice: Subject to any disclaimer, the term of this patent is extended or adjusted under 35 U.S.C. 154(b) by 4 days.

(21) Appl. No.: 13/821,938

(22) PCT Filed: Aug. 11, 2011

(86) PCT No.: PCT/CN2011/078295
§ 371 (c)(1),
(2), (4) Date: Aug. 1, 2013

(87) PCT Pub. No.: WO2012/031518
PCT Pub. Date: Mar. 15, 2012

(65) Prior Publication Data
US 2013/0310310 A1    Nov. 21, 2013

(30) Foreign Application Priority Data
Sep. 9, 2010 (CN) .......................... 2010 1 0276918

(51) Int. Cl.
| | | |
|---|---|---|
| *C07K 17/08* | (2006.01) | |
| *A61K 38/00* | (2006.01) | |
| *A61K 38/16* | (2006.01) | |
| *A61K 38/17* | (2006.01) | |
| *A61K 38/22* | (2006.01) | |
| *A61K 47/48* | (2006.01) | |
| *C07K 14/575* | (2006.01) | |

(52) U.S. Cl.
CPC .............. *C07K 17/08* (2013.01); *A61K 38/16* (2013.01); *A61K 38/17* (2013.01); *A61K 38/1703* (2013.01); *A61K 38/1709* (2013.01); *A61K 38/22* (2013.01); *A61K 47/48* (2013.01); *A61K 47/48215* (2013.01); *C07K 14/57563* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 6,902,744 B1 * | 6/2005 | Kolterman et al. | ........... | 424/489 |
| 7,557,183 B2 * | 7/2009 | DiMarchi et al. | ............. | 530/308 |
| 7,608,692 B2 * | 10/2009 | Prickett et al. | ............. | 530/387.3 |
| 2010/0009904 A1 | 1/2010 | Lv et al. | | |

FOREIGN PATENT DOCUMENTS

| | | | |
|---|---|---|---|
| CN | 1363559 A | 8/2002 | |
| CN | 101125207 A | 2/2008 | |
| CN | 101463078 A | 6/2009 | |
| KR | 20070115602 A | 12/2007 | |
| WO | 2006074600 A1 | 7/2006 | |
| WO | 2008130066 A1 | 10/2008 | |
| WO | WO/2008/130066 | * 10/2008 | ............. A61K 38/17 |

OTHER PUBLICATIONS

Tsubery H. et al., Prolonging the Action of Protein and Peptide Drugs by a Novel Approach of Reversible Polyethylene Glycol Modification:, Journal of Biological Chemistry, American Society for Biochemistry and Molecular Biology, U.S., vol. 279, No. 37 (Sep. 10, 2004), pp. 38118-38124.

Extended European Search Report dated Mar. 25, 2014, issued for corresponding European Patent Application No. EP 11823041.6.

Chae, S.Y. et al., "Biochemical, pharmaceutical and therapeutic properties of long-acting lithocholic acid derivatized exendin-4 analogs", Journal of Controlled Release (2009) pp. 206-213; journal homepage: www.elsevier.com/locate/jconrel.

International Search Report mailed Nov. 24, 2011 (PCT/CN2011/078295); ISA/CN.

Daniel J Drucker, Biologic actions and therapeutic potential of the proglucagon-derived peptides, Nature Clinical Practice Endocrinology & Metabolism, Nov. 2005, vol. 1, No. 1; 22-31.

EPO Communication for EP 11823041.6 mailed Sep. 15, 2015, including pending EP claims, 10 pages.

* cited by examiner

*Primary Examiner* — Marcela M Cordero Garcia
*Assistant Examiner* — Catherine Mader
(74) *Attorney, Agent, or Firm* — Banner & Witcoff, Ltd.

(57) ABSTRACT

Disclosed are PEG-modified Exendin-4 analogs and uses thereof. In particular, disclosed are PEG-modified Exendin-4 analogs as shown in formula (I), i.e., PEG-M-X-(Ex-4), or pharmaceutically acceptable salts thereof, as well as Exendin-4 analogs as shown in formula (II), i.e., [Aa$^P$]Exendin-4, wherein the symbols are as defined in the specification. Further disclosed are methods for preparing PEG-modified Exendin-4 analogs, uses of PEG-modified Exendin-4 analogs, compositions comprising the same, as well as use of the Exendin-4 analogs in the preparation of the PEG-modified Exendin-4 analogs. In the PEG-modified Exendin-4 analogs, modification by polyethylene glycol occurs in a site-directed manner in the peptide chains of the Exendin-4 analogs. The PEG-modified Exendin-4 analogs can be used to prevent and/or treat diseases and/or symptoms related to decreased activity of GLP-1 receptors, such as type II diabetes.

15 Claims, No Drawings

SEQUENCE LISTING

<160> NUMBER OF SEQ ID NOS: 2

<210> SEQ ID NO 1
<211> LENGTH: 39
<212> TYPE: PRT
<213> ORGANISM: Heloderma suspectum

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (21)..(23)
<223> OTHER INFORMATION: Xaa is Cys, Thp, Ala, Arg, Asn, Asp, Gln, Glu,
    Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (21)..(38)
<223> OTHER INFORMATION: One of positions 21-23, 27, 31 and 36-38 is Cys
    or Thp
<220> FEATURE:
<221> NAME/KEY: MISC_FEATURE
<222> LOCATION: (27)..(27)
<223> OTHER INFORMATION: Xaa is Cys, Thp, Ala, Arg, Asn, Asp, Gln, Glu,
    Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (31)..(31)
<223> OTHER INFORMATION: Xaa is Cys, Thp, Ala, Arg, Asn, Asp, Gln, Glu,
    Gly, His, Ile, Leu, Lys, Met, Phe, Pro, Ser, Thr, Trp, Tyr, or Val
<220> FEATURE:
<221> NAME/KEY: MISC_FEATURE
<222> LOCATION: (36)..(38)
<223> OTHER INFORMATION: Xaa is Cys, Thp, Ala, Arg, Asn, Asp, Gln, Glu,
    Gly, His, Ile, Leu, Lys, Met, Phe, Pro, Ser, Thr, Trp, Tyr, or Val

<400> SEQUENCE: 2

His Gly Glu Gly Thr Phe Thr Ser Asp Leu Ser Lys Gln Met Glu Glu
1               5                   10                  15

Glu Ala Val Arg Xaa Xaa Xaa Glu Trp Leu Xaa Asn Gly Gly Xaa Ser
            20                  25                  30

Ser Gly Ala Xaa Xaa Xaa Ser
        35

SITE-DIRECTED PEG-MODIFIED EXENDIN-4 ANALOGS AND USES THEREOF

CROSS REFERENCE TO RELATED APPLICATIONS

The present application is a U.S. National Phase filing of International Application No. PCT/CN2011/078295, filed on Aug. 11, 2011, designating the United States of America and claiming priority to Chinese Patent Application No. 201010276918.0, filed Sep. 9, 2010. The present application claims priority to and the benefit of all the above-identified applications, and all the above-identified applications are incorporated by reference herein in their entireties.

This application incorporates by reference the contents of a 1000 byte text file created on Jul. 18, 2013 and named IEC110033 ST25 sequencelisting.txt," which is the sequence listing for this application.

TECHNICAL FIELD

The present invention relates to site-directed PEG-modified Exendin-4 analogs, methods for preparing the same, pharmaceutical compositions comprising the same, precursors for the same, and uses thereof in the treatment of diseases such as Type II diabetes.

BACKGROUND

Exendin-4 is a natural product isolated and identified from the saliva of the Gila monster (*Heloderma suspectum*). It is a 39-amino acid peptide, whose sequence is His$^1$-Gly-Glu-Gly-Thr$^5$-Phe-Thr-Ser-Asp-Leu$^{10}$-Ser-Lys-Gln-Met-Glu$^{15}$-Glu-Glu-Ala-Val-Arg$^{20}$-Leu-Phe-Ile-Glu-Trp$^{25}$-Leu-Lys-Asn-Gly-Gly$^{30}$-Pro-Ser-Ser-Gly-Ala$^{35}$-Pro-Pro-Pro-Ser$^{39}$-NH$_2$ (SEQ ID NO: 1). Exendin-4 is an analog of glucagon-like peptide-1 (GLP-1). It is a GLP-1 receptor agonist which can activate GLP-1 receptor, and has biological activities such as the activities of controlling glyceride, promoting insulin secretion, reducing circulating glucagons, enhancing pancreatic β-cell quality, inhibiting gastric emptying, reducing intake of nutrition, and increasing sensitivity to insulin. Exendin-4 can simulate the hormones secreted in vivo naturally and therefore help regulate blood sugar level in human bodies. Moreover, it would stop exerting the role when it is not needed in patients. Another characteristic of Exendin-4 lies in the recovery of the first phase of secretion of β cells responsible for insulin secretion. The first phase of secretion refers to insulin secretion induced by food intake. However, patients with Type II diabetes lose the ability to raise such a response early in the course of the disease. Exendin-4 can not only reduce blood sugar, but also enhance the losing cellular functions, and thus is a great progress for the treatment of Type II diabetes.

Exendin-4 is approved by US FDA in April, 2005 for improving glycemic control in patients with Type II diabetes, when glycemic control is not ideal by using dimethyl-diguanide and sulfonylurea drugs. It is shown in clinical results that Exendin-4 has a significant therapeutic effect on the treatment of diabetes and has small side-effect, but brings about inconvenience to patients due to two subcutaneous administrations per day.

Due to the efficacy and the unique blood glucose-dependent mechanism of Exendin-4, it is more suitable for the preparation of a sustained-release formulation. The sustained-release injection Exendin-4 LAR, a product developed by Amylin Co. co-operated with Alkennes Co. in May, 2000, has finished phase II clinical trial, and the results show that after 15 weeks, the medicament in each of the two dose levels was well tolerated, and both the blood concentrations of Exendin-4 reached the therapeutic range as expected. Meanwhile, since Exendin-4 has a significant advantage in terms of the therapeutic mechanism of Type II diabetes, the development of its long-acting analogs also becomes a research and development hotspot in many foreign pharmaceutical companies.

Studies show that polypeptide drugs can still maintain good bioactivity after modified by polyethylene glycol (PEG), and such modification can significantly prolong in vivo half-life in organisms. Currently, there are reports on PEG-modification of Exendin-4, in which the products having PEG modified at the amino group of His$^1$, Lys$^{12}$ and Lys$^{27}$, respectively, are provided. In the research on metabolism in rats, it was found that their metabolic half-life was much longer than Exendin-4 (Jin Zhou et al., Eur. J. Pharma. Biopharm., 2009, 72:412-417). In addition, it was also reported that when Exendin-4 was modified by fatty acid, lithocholic acid or hyaluronic acid at ε-amino group of Lys$^{12}$ and Lys$^{27}$, single modified and double modified compounds were obtained, respectively (Su Young Chae et al., J. Control. Release, 2010, 144(1): 10-16; J. Control. Release, 2010, 142: 206-213; Biomaterials, 2010, 31:4121-4128).

However, as understood by a person skilled in the art, no matter Exendin-4 is modified by PEG, or by fatty acid, lithocholic acid or hyaluronic acid, there is a problem concerning poor specificity to the modification sites. Thus, the product resulted from the modification might be a mixture of different compounds modified at different single sites, which is quite disadvantageous for the subsequent pharmaceutical application.

Therefore, there is still need in the art to provide a method for site-directed modification of Exendin-4 whilst maintaining the biological activity of Exendin-4, and provide the modified Exendin-4, such as PEG-modified Exendin-4, in order to address the problem concerning poor specificity to modification of Exendin-4, such as PEG-modification of Exendin-4.

Contents of the Invention

The technical problem to be solved by the present invention is to overcome the shortcoming of poor specificity of modification of Exendin-4, such as PEG-modification of Exendin-4, and to provide a method for site-directed modification of Exendin-4 whilst maintaining the biological activity of Exendin-4, and a modified Exendin-4, such as a PEG-modified Exendin-4. The inventors surprisingly found that Exendin-4 analogs, obtained by substituting an individual amino acid of Exendin-4 with another amino acid, showed good reaction specificity during PEG-chemical modification. Moreover, the inventors found that after PEG-modification of the Exendin-4 analogs according to the present invention, the products with PEG modification had agonistic activity of GLP-1 receptor. The present invention is accomplished based on the above discoveries.

SUMMARY OF THE INVENTION

In the first aspect, the present invention provides a PEG-modified Exendin-4 analog as shown in Formula (I):

PEG-M-X-(Ex-4)     (I)

or a pharmaceutically acceptable salt thereof, wherein each symbol has the meaning as defined in the specification.

In the second aspect, the present invention provides an Exendin-4 analog as shown in Formula (II):

[Aa$^p$] Exendin-4    (II)

wherein each symbol has the meaning as defined in the specification.

In the third aspect, the present invention provides a method for preparing the PEG-modified Exendin-4 analog according to the first aspect of the present invention.

In the fourth aspect, the present invention provides a method for preparing the Exendin-4 analog according to the second aspect of the present invention.

In the fifth aspect, the present invention provides a use of the PEG-modified Exendin-4 analog according to any item of the first aspect of the present invention in the preparation of a medicament.

In the sixth aspect, the present invention provides a composition comprising a prophylactically and/or therapeutically effective amount of the PEG-modified Exendin-4 analog according to the first aspect of the present invention, and optionally a pharmaceutically acceptable carrier.

In the seventh aspect, the present invention provides a use of the Exendin-4 analog according to the second aspect of the present invention in the preparation of the PEG-modified Exendin-4 analog according to the first aspect of the present invention.

In the eighth aspect, the present invention provides a method for activating GLP-1 receptor and a method for treating relevant diseases or symptoms in a subject in need thereof.

In the ninth aspect, the present invention provides the PEG-modified Exendin-4 analog according to the first aspect of the present invention, for use as a GLP-1 receptor agonist or a prophylactical and/or therapeutic agent of diseases or symptoms.

In the tenth aspect, the present invention provides a composition for activating GLP-1 receptor in a subject in need thereof, or a composition for preventing and/or treating diseases and/or symptoms associated with low activity of GLP-1 receptor, comprising the PEG-modified Exendin-4 analog according to the first aspect of the present invention.

DETAILED DESCRIPTION OF THE INVENTION

In the first aspect, the present invention provides a PEG-modified Exendin-4 analog as shown in Formula (I):

PEG-M-X-(Ex-4)    (I)

or a pharmaceutically acceptable salt thereof, wherein,
PEG represents $RO(CH_2CH_2O)_n$—$CH_2CH_2$—, wherein R is H or $CH_3$, n is an integer of 25-2500;
M represents

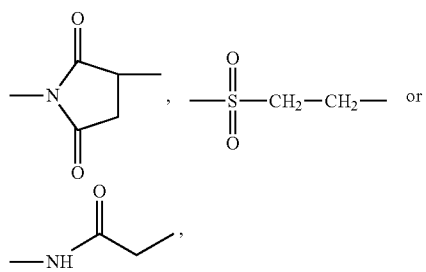

and is linked to a PEG moiety by the nitrogen or sulfur atom of each of them on one side, and is linked to the hydrosulfuryl of X moiety on the other side;

X-(Ex-4) represents a Exendin-4 analog having the following structure: His-Gly-Glu-Gly-Thr-Phe-Thr-Ser-Asp-Leu-Ser-Lys-Gln-Met-Glu-Glu-Glu-Ala-Val-Arg-$Aa_{21}$-$Aa_{22}$-$Aa_{23}$-Glu-Trp-Leu-$Aa_{27}$-Asn-Gly-Gly-$Aa_{31}$-Ser-Ser-Gly-Ala-$Aa_{36}$-$Aa_{37}$-$Aa_{38}$-Ser-$NH_2$ (SEQ ID NO:2), wherein $Aa_{21}$, $Aa_{22}$, $Aa_{23}$, $Aa_{27}$, $Aa_{31}$, $Aa_{36}$, $Aa_{37}$ and $Aa_{38}$ each are independently selected from the following amino acids: Cys, Thp, Ala, Arg, Asn, Asp, Gln, Glu, Gly, His, Ile, Leu, Lys, Met, Phe, Pro, Ser, Thr, Trp, Tyr, Val, and one of $Aa_{21}$, $Aa_{22}$, $Aa_{23}$, $Aa_{27}$, $Aa_{31}$, $Aa_{36}$, $Aa_{37}$ and $Aa_{38}$ is Cys or Thp;

X represents an amino acid at position 21, 22, 23, 27, 31, 36, 37 or 38 that is cysteine or 4-thioproline (Thp,

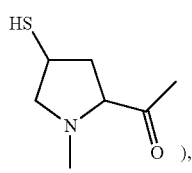), in the Exendin-4 analog as shown in X-(Ex-4), wherein the hydrosulfuryl of the amino acid is linked to M moiety.

In addition, or according to the first aspect, the present invention further provides in the first aspect a PEG-modified Exendin-4 analog as shown in Formula (I):

PEG-M-X-(Ex-4)    (I)

or a pharmaceutically acceptable salt thereof, wherein,
PEG represents polyethylene glycol with a molecular weight of 1,000-100,000;
M represents

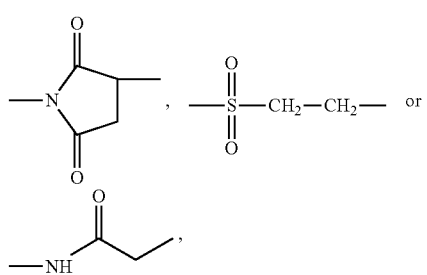

and is linked to a PEG moiety by the nitrogen or sulfur atom of each of them on one side, and is linked to the hydrosulfuryl of X moiety on the other side;

X-(Ex-4) represents a 39-amino acid peptide, wherein an amino acid is substituted by cysteine or 4-thioproline (Thp,

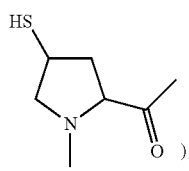)

at position 21, 22, 23, 27, 31, 36, 37 or 38 of His-Gly-Glu-Gly-Thr-Phe-Thr-Ser-Asp-Leu-Ser-Lys-Gln-Met-Glu-Glu-Glu-Ala-Val-Arg-Leu$^{21}$-Phe$^{22}$-Ile$^{23}$-Glu-Trp-Leu-Lys$^{27}$-Asn-Gly-Gly-Pro$^{31}$-Ser-Ser-Gly-Ala-Pro$^{36}$-Pro$^{37}$-Pro$^{38}$-Ser-$NH_2$;

X represents an amino acid at position 21, 22, 23, 27, 31, 36, 37 or 38 that is cysteine or 4-thioproline (Thp,

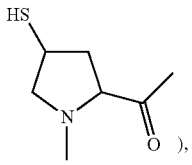

), in the 39-amino acid peptide as shown in X-(Ex-4), wherein the hydrosulfuryl of the amino acid is linked to M moiety.

Preferably, in the PEG-modified Exendin-4 analog according to any item of the first aspect of the present invention, the PEG represents RO(CH$_2$CH$_2$O)$_n$—CH$_2$CH$_2$—, wherein R is H or CH$_3$, n is an integer of 50-2000. In one embodiment, R is H. In one embodiment, R is CH$_3$. In one embodiment, n is an integer of 50-1500. In one embodiment, n is an integer of 50-1000. In one embodiment, n is an integer of 75-1500. In one embodiment, n is an integer of 75-1000. In one embodiment, n is an integer of 75-500. In one embodiment, n is an integer of 100-500.

Preferably, in the PEG-modified Exendin-4 analog according to any item of the first aspect of the present invention, the PEG represents polyethylene glycol with a molecular weight of 1,000-100,000. In one embodiment, the PEG represents polyethylene glycol with a molecular weight of 2,000-80,000. In one embodiment, the PEG represents polyethylene glycol with a molecular weight of 3,000-60,000. In one embodiment, the PEG represents polyethylene glycol with a molecular weight of 4,000-60,000. In one embodiment, the PEG represents polyethylene glycol with a molecular weight of 5,000-60,000. In one embodiment, the PEG represents polyethylene glycol with a molecular weight of 3,000-50,000. In one embodiment, the PEG represents polyethylene glycol with a molecular weight of 4,000-40,000. In one embodiment, the PEG represents polyethylene glycol with a molecular weight of 4,000-30,000. In one embodiment, the PEG represents polyethylene glycol with a molecular weight of 5,000-20,000.

Preferably, in the PEG-modified Exendin-4 analog according to any item of the first aspect of the present invention, M represents

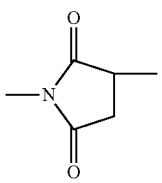

(in the present invention, it may be represented by MAL),

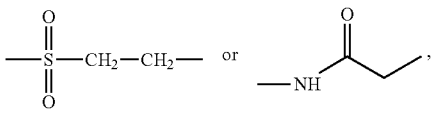

and is linked to a PEG moiety by the nitrogen or sulfur atom of each of them on one side, and is linked to the hydrosulfuryl of X moiety on the other side. For example, they form

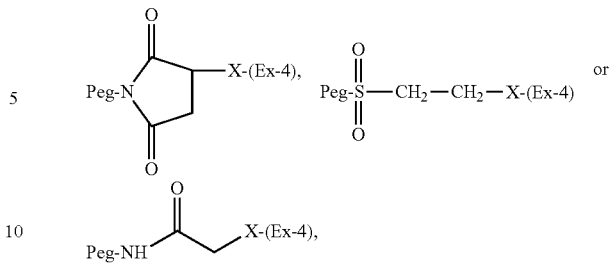

respectively, wherein the Peg in each of the formulae represents polyethylene glycol as defined in the specification. In one embodiment, M represents

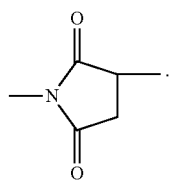

Preferably, in the PEG-modified Exendin-4 analog according to any item of the first aspect of the present invention, X-(Ex-4) represents a Exendin-4 analog having the following structure: His-Gly-Glu-Gly-Thr-Phe-Thr-Ser-Asp-Leu-Ser-Lys-Gln-Met-Glu-Glu-Glu-Ala-Val-Arg-Aa$_{21}$-Aa$_{22}$-Aa$_{23}$-Glu-Trp-Leu-Aa$_{27}$-Asn-Gly-Gly-Aa$_{31}$-Ser-Ser-Gly-Ala-Aa$_{36}$-Aa$_{37}$-Aa$_{38}$-Ser-NH$_2$ (SEQ ID NO:2), wherein Aa$_{21}$, Aa$_{22}$, Aa$_{23}$, Aa$_{27}$, Aa$_{31}$, Aa$_{36}$, Aa$_{37}$ and Aa$_{38}$ each are independently selected from the following amino acids: Cys, Thp, Leu, Phe, Ile, Lys, Pro; and one of Aa$_{21}$, Aa$_{22}$, Aa$_{23}$, Aa$_{27}$, Aa$_{31}$, Aa$_{36}$, Aa$_{37}$ and Aa$_{38}$ is Cys or Thp. In one embodiment, the Aa$_{21}$ is selected from the group consisting of Cys, Thp and Leu, the Aa$_{22}$ is selected from the group consisting of Cys, Thp and Phe, the Aa$_{23}$ is selected from the group consisting of Cys, Thp and Ile, the Aa$_{27}$ is selected from the group consisting of Cys, Thp and Lys, the Aa$_{31}$ is selected from the group consisting of Cys, Thp and Pro, the Aa$_{36}$ is selected from the group consisting of Cys, Thp and Pro, the Aa$_{37}$ is selected from the group consisting of Cys, Thp and Pro, the Aa$_{38}$ is selected from the group consisting of Cys, Thp and Pro; provided that only one of Aa$_{21}$, Aa$_{22}$, Aa$_{23}$, Aa$_{27}$, Aa$_{31}$, Aa$_{36}$, Aa$_{37}$ and Aa$_{38}$ is Cys or Thp.

Preferably, in the PEG-modified Exendin-4 analog according to any item of the first aspect of the present invention, X represents an amino acid at position 21, 22, 23, 27, 31, 36, 37 or 38 that is cysteine or 4-thioproline, in the Exendin-4 analogs as shown in X-(Ex-4), and the hydrosulfuryl of the amino acid is linked to M group. In one embodiment, X represents an amino acid at position 21, 22, 23, 31, 36, 37 or 38 that is cysteine or 4-thioproline, in the Exendin-4 analogs as shown in X-(Ex-4). In one embodiment, X represents an amino acid at position 21, 22, 23, 31, 36, 37 or 38 that is cysteine, in the Exendin-4 analogs as shown in X-(Ex-4). In one embodiment, X represents an amino acid at position 31, 36, 37 or 38 that is 4-thioproline, in the Exendin-4 analogs as shown in X-(Ex-4).

Preferably, in the PEG-modified Exendin-4 analog according to any item of the first aspect of the present invention, X-(Ex-4) represents a 39-amino acid peptide in which an amino acid is substituted by cysteine (i.e. Cys) or 4-thioproline (i.e. Thp or

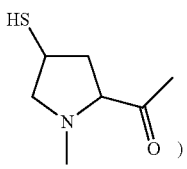

at position 21, 22, 23, 27, 31, 36, 37 or 38 of His-Gly-Glu-Gly-Thr-Phe-Thr-Ser-Asp-Leu-Ser-Lys-Gln-Met-Glu-Glu-Glu-Ala-Val-Arg-Leu$^{21}$-Phe$^{22}$-Ile$^{23}$-Glu-Trp-Leu-Lys$^{27}$-Asn-Gly-Gly-Pro$^{31}$-Ser-Ser-Gly-Ala-Pro$^{36}$-Pro$^{37}$-Pro$^{38}$-Ser-NH$_2$ (SEQ ID NO:1). In one embodiment, Aa$_{21}$ is selected from the group consisting of Cys and Thp. In one embodiment, Aa$_{22}$ is selected from the group consisting of Cys and Thp. In one embodiment, Aa$_{23}$ is selected from the group consisting of Cys and Thp. In one embodiment, Aa$_{27}$ is selected from the group consisting of Cys and Thp. In one embodiment, Aa$_{31}$ is selected from the group consisting of Cys, and Thp. In one embodiment, Aa$_{36}$ is selected from the group consisting of Cys and Thp. In one embodiment, Aa$_{37}$ is selected from the group consisting of Cys and Thp. In one embodiment, Aa$_{38}$ is selected from the group consisting of Cys and Thp.

Preferably, in the PEG-modified Exendin-4 analog according to any item of the first aspect of the present invention, X represents an amino acid at position 21, 22, 23, 27, 31, 36, 37 or 38 that is cysteine or 4-thioproline, in the 39-amino acid peptide as shown in X-(Ex-4), wherein the hydrosulfuryl of the amino acid is linked to M group. In one embodiment, X represents an amino acid at position 21, 22, 23, 31, 36, 37 or 38 that is cysteine or 4-thioproline, in the 39-amino acid peptide as shown in X-(Ex-4). In one embodiment, X represents an amino acid at position 21, 22, 23, 31, 36, 37 or 38 that is cysteine, in the 39-amino acid peptide as shown in X-(Ex-4). In one embodiment, X represents an amino acid at position 31, 36, 37 or 38 that is 4-thioproline, in the 39-amino acid peptide as shown in X-(Ex-4).

Preferably, the PEG-modified Exendin-4 analog according to any item of the first aspect of the present invention is a site-directed PEG-modified Exendin-4 analog or a pharmaceutically acceptable salt thereof. Preferably, the PEG-modified Exendin-4 analog according to any item of the first aspect of the present invention is a site-directed PEG-modified Exendin-4 analog or a pharmaceutically acceptable salt thereof, wherein the PEG modification is a single PEG modification.

Preferably, the PEG-modified Exendin-4 analog according to any item of the first aspect of the present invention is selected from the group consisting of
  [Cys$^{21}$(mPEG$_{5000}$-MAL)] Exendin-4,
  [Cys$^{22}$(mPEG$_{5000}$-MAL)] Exendin-4,
  [Cys$^{23}$(mPEG$_{5000}$-MAL)] Exendin-4,
  [Cys$^{31}$(mPEG$_{5000}$-MAL)] Exendin-4,
  [Cys$^{36}$(mPEG$_{5000}$-MAL)] Exendin-4,
  [Cys$^{37}$(mPEG$_{5000}$-MAL)] Exendin-4,
  [Cys$^{38}$(mPEG$_{5000}$-MAL)] Exendin-4,
  [Thp$^{31}$(mPEG$_{5000}$-MAL)] Exendin-4,
  [Thp$^{36}$(mPEG$_{5000}$-MAL)] Exendin-4,
  [Thp$^{37}$(mPEG$_{5000}$-MAL)] Exendin-4,
  [Thp$^{38}$(mPEG$_{5000}$-MAL)] Exendin-4, and
  [Cys$^{31}$(mPEG$_{20000}$-MAL)] Exendin-4,
  or a pharmaceutically acceptable salt thereof.

In the compounds as shown in the above-mentioned formulae, for example, as to the compound as shown in [Cys$^{21}$(mPEG$_{5000}$-MAL)] Exendin-4, Cys$^{21}$ indicates that the amino acid Leu at position 21 of Exendin-4 is substituted with Cys, and therefore the 39-amino acid peptide is a Exendin-4 analog in which the amino acid at position 21 is Cys; mPEG$_{5000}$ represents polyethylene glycol with a molecular weight of about 5000 having methyl (represented by m) at the end; MAL represents

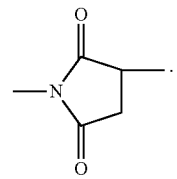

That is, [Cys$^{21}$(mPEG$_{5000}$-MAL)] Exendin-4 represents a PEG-modified Exendin-4 analog wherein the Exendin-4 analog having the amino acid at position 21 substituted with Cys is linked to polyethylene glycol with a molecular weight of about 5000 via MAL, wherein MAL is linked to PEG moiety by the nitrogen atom on one side, and is linked to the hydrosulfuryl of Cys on the other side. Other formulae have similar meanings.

In the second aspect, the present invention provides an Exendin-4 analog as show in Formula (II):

[Aa$^p$] Exendin-4     (II)

wherein

Exendin-4 represents a 39-amino acid peptide, i.e. His-Gly-Glu-Gly-Thr-Phe-Thr-Ser-Asp-Leu-Ser-Lys-Gln-Met-Glu-Glu-Glu-Ala-Val-Arg-Leu$^{21}$-Phe$^{22}$-Ile$^{23}$-Glu-Trp-Leu-Lys$^{27}$-Asn-Gly-Gly-Pro$^{31}$-Ser-Ser-Gly-Ala-Pro$^{36}$-Pro$^{37}$-Pro$^{38}$-Ser-NH$_2$ (SEQ ID NO:1);

Aa$^p$ represents an amino acid for substituting the amino acid at p position of the 39-amino acid peptide as shown in Exendin-4, which is selected from cysteine (i.e. Cys) or 4-thioproline (i.e. Thp,

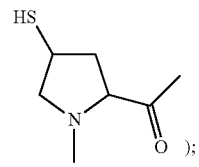

and p represents position 21, 22, 23, 27, 31, 36, 37 or 38 of the 39-amino acid peptide as shown in Exendin-4.

In the Exendin-4 analog according to any item of the second aspect of the present invention, preferably,
  Aa$^p$ represents cysteine for substituting the amino acid at p position of the 39-amino acid peptide shown in Exendin-4;
  p represents position 21, 22, 23, 31, 36, 37 or 38 of the 39-amino acid peptide shown in Exendin-4.
  Preferably, in the Exendin-4 analog according to any item of the second aspect of the present invention,
  Aa$^p$ represents 4-thioproline for substituting the amino acid at p position of the 39-amino acid peptide shown in Exendin-4;
  p represents position 31, 36, 37 or 38 of the 39-amino acid peptide shown in Exendin-4.
  Preferably, the Exendin-4 analog according to any item of the second aspect of the present invention is selected from the group consisting of

[Cys$^{21}$] Exendin-4,
[Cys$^{22}$] Exendin-4,
[Cys$^{23}$] Exendin-4,
[Cys$^{31}$] Exendin-4,
[Cys$^{36}$] Exendin-4,
[Cys$^{37}$] Exendin-4,
[Cys$^{38}$] Exendin-4,
[Thp$^{31}$] Exendin-4,
[Thp$^{36}$] Exendin-4,
[Thp$^{37}$] Exendin-4, and
[Thp$^{38}$] Exendin-4.

In the compounds shown in the above formulae, for example, as to the compound shown in [Cys$^{21}$] Exendin-4, Cys$^{21}$ means that the amino acid Leu at position 21 of Exendin-4 is substituted with Cys, and thus the 39-amino acid peptide shown in the Exendin-4 is an Exendin-4 analog having Cys at position 21. That is, [Cys$^{21}$] Exendin-4 represents such a compound, i.e. Exendin-4 having the amino acid at position 21 substituted with Cys. Other formulae have similar meanings.

In the third aspect, the present invention provides a method for preparing the PEG-modified Exendin-4 analog according to any item of the first aspect of the present invention, comprising the step of reacting the Exendin-4 analog according to any item of the second aspect of the present invention with PEG-M. In one embodiment, the reaction is carried out in a phosphate buffer. In one embodiment, the reaction is carried out at a temperature of 10-40° C. (such as 15-35° C., such as room temperature). In one embodiment, the PEG-M is PEG-MAL.

In one embodiment of the method according to any item of the third aspect of the present invention, the Exendin-4 analog is prepared through the following steps: (1) synthesizing peptide resin on the basis of the amino acid sequence of the Exendin-4 analog to be obtained, by the standard Fmoc Solid-phase synthetic method, wherein Rink-amide resin is used as the solid-phase carrier, HBTU-HOBt is used as condensing agent, the corresponding Fmoc-protected amino acids are used as raw material; (2) removing the protective groups of the peptide and cleaving the peptide from the resin at 0-40° C. (for example, reacting at about 0° C. for about 30 min, and then reacting at room temperature for 90 min), wherein a mixture of trifluoroacetic acid: thioanisole: metacresol: dithioglycol: water (for example, in a volume ratio of 8.25: 0.5:0.5:0.25:0.5) is used as the cleavage solution; and (3) optionally a purification step.

Therefore, in the four aspect, the present invention provides a method for preparing the Exendin-4 analog according to any item of the second aspect of the present invention, comprising the following steps: (1) synthesizing peptide resin based on the amino acid sequence of the Exendin-4 analog to be obtained, by the standard Fmoc Solid-phase synthetic method, wherein Rink-amide resin is used as the solid-phase carrier, HBTU-HOBt is used as condensing agent, the corresponding Fmoc-protected amino acids are used as raw material; (2) removing the protective groups of the peptide and cleaving the peptide from the resin at 0-40° C. (for example, reacting at about 0° C. for about 30 min, and then reacting at room temperature for 90 min, wherein a mixture of trifluoroacetic acid: thioanisole: metacresol: dithioglycol: water (for example, in a volume ratio of 8.25:0.5:0.5:0.25:0.5) is used as the cleavage solution; and (3) optionally a purification step.

In the fifth aspect, the present invention provides a use of the PEG-modified Exendin-4 analog according to any item of the first aspect of the present invention in the preparation of a medicament as GLP-1 receptor agonist.

In the fifth aspect, the present invention also provides a use of the PEG-modified Exendin-4 analog according to any item of the first aspect of the present invention in the preparation of a medicament for preventing and/or treating diseases and/or symptoms associated with low activity of GLP-1 receptor. In one embodiment, the PEG-modified Exendin-4 analog may be useful for controlling glyceride, promoting insulin secretion, reducing circulating glucagons, enhancing pancreatic β-cell quality, inhibiting gastric emptying, reducing intake of nutrition, and increasing sensitivity to insulin, so as to prevent and/or treat diseases and/or symptoms associated with low activity of GLP-1 receptor.

In the fifth aspect, the present invention also provides a use of the PEG-modified Exendin-4 analog according to any item of the first aspect of the present invention in the preparation of a medication for preventing and/or treating diseases and/or symptoms associated with glucose metabolism. In one embodiment, the diseases and/or symptoms associated with glucose metabolism are selected from the group consisting of Type II diabetes, obesity and/or adiposity, and hypofunction of β cells.

In the fifth aspect, the present invention also provides a use of the PEG-modified Exendin-4 analog according to any item of the first aspect of the present invention in the preparation of a medication for in vivo glycemic control in a patient suffering from Type II diabetes.

In the sixth aspect, the present invention provides a composition comprising a prophylactically and/or therapeutically effective amount of the PEG-modified Exendin-4 analog according to any item of the first aspect of the present invention, and optionally a pharmaceutically acceptable carrier.

In the seventh aspect, the present invention provides a use of the Exendin-4 analog according to any item of the second aspect of the present invention in the preparation of the PEG-modified Exendin-4 analog according to any item of the first aspect of the present invention.

In the eighth aspect, the present invention provides a method for activating GLP-1 receptor in a subject in need thereof, comprising administering a prophylactically and/or therapeutically effective amount of the PEG-modified Exendin-4 analog according to any item of the first aspect of the present invention to the subject.

In the eighth aspect, the present invention also provides a method of preventing and/or treating diseases and/or symptoms associated with low activity of GLP-1 receptor in a subject in need thereof, comprising administering a prophylactically and/or therapeutically effective amount of the PEG-modified Exendin-4 analog according to any item of the first aspect of the present invention to the subject. In one embodiment, the present invention provides a method for controlling glyceride, promoting insulin secretion, reducing circulating glucagons, enhancing pancreatic β-cell quality, inhibiting gastric emptying, reducing intake of nutrition, and/or increasing sensitivity to insulin in a subject in need thereof, comprising administering a prophylactically and/or therapeutically effective amount of the PEG-modified Exendin-4 analog according to any item of the first aspect of the present invention to the subject. The method of the present invention is useful for the prevention and/or treatment of diseases and/or symptoms associated with low activity of GLP-1 receptor.

In the eighth aspect, the present invention also provides a method for preventing and/or treating diseases and/or symptoms associated with glucose metabolism in a subject in need thereof, comprising administering a prophylactically and/or therapeutically effective amount of the PEG-modified Exendin-4 analog according to any item of the first aspect of the present invention to the subject. In one embodiment, the diseases and/or symptoms associated with glucose metabolism are selected from the group consisting of Type II diabetes, obesity and/or adiposity, and hypofunction of β cells.

In the eighth aspect, the present invention also provides a method for glycemic control in a subject in need thereof, comprising administering a prophylactically and/or therapeutically effective amount of the PEG-modified Exendin-4 analog according to any item of the first aspect of the present invention to the subject. In one embodiment, the subject is suffering from Type II diabetes.

In the ninth aspect, the present invention provides the PEG-modified Exendin-4 analog according to any item of the first aspect of the present invention, for use as GLP-1 receptor agonist.

In the ninth aspect, the present invention also provides the PEG-modified Exendin-4 analog according to any item of the first aspect of the present invention, for use in preventing and/or treating diseases and/or symptoms associated with low activity of GLP-1 receptor. In one embodiment, the present invention provides the PEG-modified Exendin-4 analog according to any item of the first aspect of the present invention, for use in controlling glyceride, promoting insulin secretion, reducing circulating glucagons, enhancing pancreatic β-cell quality, inhibiting gastric emptying, reducing intake of nutrition, and/or increasing sensitivity to insulin.

In the ninth aspect, the present invention also provides the PEG-modified Exendin-4 analog according to any item of the first aspect of the present invention, for use in preventing and/or treating diseases and/or symptoms associated with glucose metabolism. In one embodiment, the diseases and/or symptoms associated with glucose metabolism are selected from the group consisting of Type II diabetes, obesity and/or adiposity, and hypofunction of β cells.

In the ninth aspect, the present invention also provides the PEG-modified Exendin-4 analog according to any item of the first aspect of the present invention for use in glycemic control in a patient suffering from Type II diabetes.

In the tenth aspect, the present invention provides a composition for activating GLP-1 receptor in a subject in need thereof, comprising the PEG-modified Exendin-4 analog according to any item of the first aspect of the present invention.

In the tenth aspect, the present invention also provides a composition for preventing and/or treating diseases and/or symptoms associated with low activity of GLP-1 receptor, comprising the PEG-modified Exendin-4 analog according to any item of the first aspect of the present invention. In one embodiment, the present invention provides a composition for controlling glyceride, promoting insulin secretion, reducing circulating glucagons, enhancing pancreatic β-cell quality, inhibiting gastric emptying, reducing intake of nutrition, and/or increasing sensitivity to insulin, comprising the PEG-modified Exendin-4 analog according to any item of the first aspect of the present invention.

In the tenth aspect, the present invention also provides a composition for preventing and/or treating diseases and/or symptoms associated with glucose metabolism in a subject in need thereof, comprising the PEG-modified Exendin-4 analog according to any item of the first aspect of the present invention. In one embodiment, the diseases and/or symptoms associated with glucose metabolism are selected from the group consisting of Type II diabetes, obesity and/or adiposity, and hypofunction of β cells.

In the tenth aspect, the present invention also provides a composition for glycemic control in a subject in need thereof, comprising the PEG-modified Exendin-4 analog according to any item of the first aspect of the present invention. In one embodiment, the subject is suffering from Type II diabetes.

The characteristics possessed by any aspect of the present invention or any item thereof are also applied to any other aspect or any item thereof, as long as they do not contradict each other. Of course, when applying the characteristics of one aspect or any item thereof to another aspect or any item thereof, the corresponding characteristics may be appropriately modified if necessary. In the present invention, for example, when referring to "any item of the first aspect of the present invention", the "any item" refers to any sub-aspect of the first aspect of the present invention; and it has the same meaning when being mentioned in other aspects in a similar manner.

Various aspects and characteristics of the present invention are further described as follows.

The entire contents of all the documents as cited in the present invention are incorporated herein by reference, and if the meanings expressed in these documents are inconsistent with those of the present invention, the expressions of the present invention will control. In addition, various terms and phrases used in the present invention have the general meanings recognized by a person skilled in the art. Even so, it is still intended to better expound and explain these terms and phrases in the present invention. When the terms and phrases mentioned herein have the meanings different from the recognized meanings, the meanings expressed in the present invention prevail.

As used herein, the term "about", it generally refers to a error range allowable in the art, such as ±10%, such as ±5%, such as ±2%, for example, when the term is used to describe the yield of a product.

As used herein, the term "an effective amount" refers to a dose at which the diseases or disorders as described in the present invention can be treated, prevented, relieved and/or alleviated in a subject.

As used herein, the term "a pharmaceutical composition", refers to a substance useful for the treatment, prevention, relief and/or alleviation of the disease, disorders and symptoms as described in the present invention in a subject.

As used herein, the term "subject" or "patient", may refer to an animal which receives the composition and extract according to the present invention to treat, prevent, relieve and/or alleviate the diseases as described in the present invention, in particular, a mammalian, such as human, dog, monkey, cow, horse, and the like.

As used herein, the term "diseases or symptoms" refers to body states in a subject, which are associated with the diseases or symptoms as described in the present invention.

As used herein, "%", if not specially indicated, generally refers to a percentage of weight/weight when the overall material is solid, and generally refers to a percentage of weight/volume when the overall material is liquid. Of course, when the overall material is liquid and the solute is liquid, the percentage of the liquid solute is generally characterized by a percentage of volume/volume.

As described herein, the term "Exendin-4" refers to a 39-amino acid peptide having a sequence of His$^1$-Gly-Glu-Gly-Thr$^5$-Phe-Thr-Ser-Asp-Leu$^{10}$-Ser-Lys-Gln-Met-Glu$^{15}$-Glu-Glu-Ala-Val-Arg$^{20}$-Leu-Phe-Ile-Glu-Trp$^{25}$-Leu-Lys-Asn-Gly-Gly$^{30}$-Pro-Ser-Ser-Gly-Ala$^{35}$-Pro-Pro-Pro-Ser$^{39}$-NH$_2$ (SEQ ID NO:1). The term "Exendin-4 analog" refers to the 39-amino acid peptide of Exendin-4 having one or more amino acid(s) (preferably one amino acid) at any positions (preferably position 21, 22, 23, 27, 31, 36, 37 or 38) substituted with other amino acid(s) (preferably cysteine or 4-thioproline).

As described herein, the term "PEG" refers to polyethylene glycol, whose size may be represented by polymerization degree (such as, in the specification, PEG may be represented as $RO(CH_2CH_2O)_n$—$CH_2CH_2$—, wherein n is an integer of 25-2500), or may also be represented by molecular weight (such as in the specification, PEG may represent as polyethylene glycol with a molecular weight of 1,000-100,000). Said two different expression modes are well known by a person skilled in the art, and do not contradict each other.

If not specially specified, all the amino acids as described in the present invention are L-amino acids.

As described herein, the term "diseases and/or symptoms associated with GLP-1 receptor" refers to the relevant diseases which are prevented and/or treated by agonizing GLP-1 receptor, and mainly refers to glucose metabolism diseases such as Type II diabetes, obesity and/or adiposity, and hypofunction of β cells.

The purpose of the present invention is to provide a class of PEG-modified exendin-4 analogs which are helpful for the development of long-acting medicaments and formations for treating Type II diabetes. The inventors found that when amino acid residues containing functional groups with reaction specificity were introduced, the reaction specificity of Exendin-4 to PEG was increased, thereby enabling the obtainment of precisely site-directed mono-PEG modified compounds. Furthermore, the properties of PEG, such as prolonging the acting time of polypeptide drugs, enhancing bioavailability and so on, enable the improvement of in vivo behaviour of Exendin-4.

One of the purposes of the present invention is to provide a site-directed PEG-modified Ex-4 analog, the structure of which is characterized in that some amino acid residues of the amino acid sequence of Ex-4 are altered to keep only one amino group, carboxyl group or hydrosulfuryl group in the side chain, so that the site-directed PEG-modification is achieved at the amino group, carboxyl group or hydrosulfuryl group. As to the PEG-modified Ex-4 analogs according to the present invention, please refer to the structure of Formula (I) and the definition thereof as described in the specification.

Another purpose of the present invention is to provide a method for preparing a PEG-modified Ex-4 analog.

The present invention also relates to a pharmaceutical composition comprising at least one of the PEGylated Ex-4 analogs or stereoisomers or salts thereof, and a pharmaceutically acceptable carrier or excipient.

The present invention also relates to a use of the compound of the present invention in the preparation of a medicament for treating and preventing diabetes.

The present invention also relates to a use of the compound of the present invention in the treatment and prevention of diabetes and diseases or symptoms associated with glucose metabolism.

In one aspect, the present invention provides a PEG-modified Exendin-4 analog as shown in Formula (I):

PEG-M-X-(Ex-4)    (I)

wherein

PEG is $RO(CH_2CH_2O)_n$—$CH_2CH_2$—, R=H or $CH_3$, n=25-2500;

M=

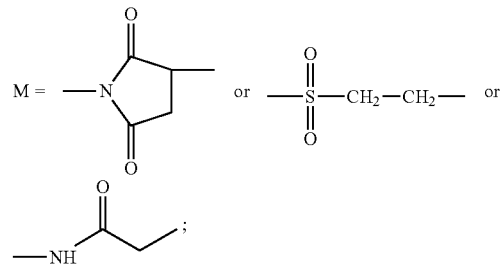

X-(Ex-4) is a Exendin-4 analog having the following structure: $His^1$-Gly-Glu-Gly-$Thr^5$-Phe-Thr-Ser-Asp-$Leu^{10}$-Ser-Lys-Gln-Met-$Glu^{15}$-Glu-Glu-Ala-Val-$Arg^{20}$-$Aa_{21}$-$Aa_{22}$-$Aa_{23}$-Glu-$Trp^{25}$-Leu-$Aa_{27}$-Asn-Gly-$Gly^{30}$-$Aa_{31}$-Ser-Ser-Gly-$Ala^{35}$-$Aa_{36}$-$Aa_{37}$-$Aa_{38}$-$Ser^{39}$-$NH_2$ (SEQ ID NO:2), wherein $Aa_{21}$, $Aa_{22}$, $Aa_{23}$, $Aa_{27}$, $Aa_{31}$, $Aa_{36}$, $Aa_{37}$ and $Aa_{38}$ each are independently selected from the group consisting of Cys, Thp, Ala, Arg, Asn, Asp, Gln, Glu, Gly, His, Ile, Leu, Lys, Met, Phe, Pro, Ser, Cys or Thp;

X represents an amino acid at position 21, 22, 23, 27, 31, 36, 37 or 38 in the Exendin-4 analog as shown in X-(Ex-4), which is cysteine or 4-thioproline (Thp,

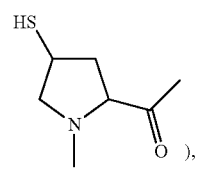

and is linked to M group via the hydrosulfuryl.

If not specially specified, all these amino acids are L-amino acids.

In one preferred embodiment of the PEG-modified Exendin-4 analog according to the present invention, X-(Ex-4) moiety of Formula (I) has the following structural characteristics:

$Aa_{21}$ may be selected from the group consisting of Cys, Thp, and Leu;

$Aa_{22}$ may be selected from the group consisting of Cys, Thp, and Phe;

$Aa_{23}$ may be selected from the group consisting of Cys, Thp, and Ile;

$Aa_{27}$ may be selected from the group consisting of Cys, Thp, and Lys;

$Aa_{31}$ may be selected from the group consisting of Cys, Thp, and Pro;

$Aa_{36}$ may be selected from the group consisting of Cys, Thp, and Pro;

$Aa_{37}$ may be selected from the group consisting of Cys, Thp, and Pro;

$Aa_{38}$ may be selected from the group consisting of Cys, Thp, and Pro;

provided that only one of $Aa_{21}$, $Aa_{22}$, $Aa_{23}$, $Aa_{27}$, $Aa_{31}$, $Aa_{36}$, $Aa_{37}$ and $Aa_{38}$ is Cys or Thp.

If not specially specified, all these amino acids are L-amino acids.

Preferably, the PEG-modified Exendin-4 analog according to the present invention is selected from the group consisting of the following 12 PEG-modified Exendin-4 analogs:

1 $[Cys^{21}(mPEG_{5000}\text{-}MAL)]$ Exendin-4
2 $[Cys^{22}(mPEG_{5000}\text{-}MAL)]$ Exendin-4
3 $[Cys^{23}(mPEG_{5000}\text{-}MAL)]$ Exendin-4
4 $[Cys^{31}(mPEG_{5000}\text{-}MAL)]$ Exendin-4
5 $[Cys^{36}(mPEG_{5000}\text{-}MAL)]$ Exendin-4
6 $[Cys^{37}(mPEG_{5000}\text{-}MAL)]$ Exendin-4
7 $[Cys^{38}(mPEG_{5000}\text{-}MAL)]$ Exendin-4
8 $[Thp^{31}(mPEG_{5000}\text{-}MAL)]$ Exendin-4
9 $[Thp^{36}(mPEG_{5000}\text{-}MAL)]$ Exendin-4
10 $[Thp^{37}(mPEG_{5000}\text{-}MAL)]$ Exendin-4
11 $[Thp^{38}(mPEG_{5000}\text{-}MAL)]$ Exendin-4
12 $[Cys^{31}(mPEG_{20000}\text{-}MAL)]$ Exendin-4

The compounds according to the present invention are prepared by conventional peptide synthetic methods, including solid-phase peptide synthetic methods, liquid-phase peptide synthetic methods, and solid phase-liquid phase peptide synthetic methods, wherein amino acids are protected using Fmoc-/tBu- or Boc-/Bzl-strategy; the amino acids are linked from N-terminal to C-terminal, or fragments are synthesized first, and then the fragments are linked; in solid-phase synthesis, various resins (such as MBHA, PAL, Rink amide resins) may be used as carrier as long as they can form amide end; various common condensing agents (such as DCC/HOBT, BOP/DIEA, HBTU/HOBt, TBTU, etc.) are used in the condensation reaction; after the reaction is finished, the peptide is cleaved from the resin by trifluoroacetic acid or anhydrous HF. The linkage of the peptide to a PEG-modification agent is carried out in an aqueous solution or phosphate buffer; the pH value of the reaction solution is appropriately controlled; the modified product is monitored, isolated and purified by RP-HPLC; and the final product is identified by MALDI-TOF-MS.

According to the present invention, a part of preferred compounds can agonize GLP-1 receptor in cellular level.

The present invention also relates to a pharmaceutical composition comprising as active component, an effective dose of at least one modified peptide and/or a steroisomer or a physiologically intoxic salt thereof, and a conventional pharmaceutical excipient or ajuvant. The "conventional pharmaceutical excipient or ajuvant" herein includes one or all solvents, dispersion mediums, coatings, antibacterial agents or antifungal agents, isotonic agents and sustained-release agents, and similar physiologically compatible agents, wherein those suitable for intravenous injection, intramuscular injection, subcutaneous injection, or other parenteral administration modes are preferable. Depending on the administration modes, the active compounds may be coated to protect the compounds from inactivation due to acids or other natural conditions.

The term "physiologically intoxic salts" as used in the present invention, refers to salts that can maintain the expected physiological activity of the parent compound without bringing about any unexpected side-effect, or a composition comprising the same, for example, hydrochloride, hydrobromide, sulfate, phosphate, nitrate, acetate, oxalate, tartrate, succinate, malate, benzoate, pamoate, alginate, mesylate, naphthalenesulfonate, etc. Based on the cations comprised in the salts, the salts may be classified into inorganic salts such as potassium salts, lithium salts, zinc salts, copper salts, barium salts, bismuth salts, calcium salts, and organic salts such as trialkyl ammonium salts.

The modified peptides of the present invention and the stereoisomers thereof or pharmaceutical compositions comprising the same may be administered in any known routes, such as oral, intramuscular, subcutaneous, and nasal administration, and the dosage form for administration includes, for example, tablets, capsules, buccal tablets, chewable tablets, elixirs, suspensions, transdermal agents, microencapsulated agents, implants, syrups, etc. They may be formulated into common formulations, sustained-release formulations, controlled-release formulations and various microparticle drug delivery systems. In order to formulate a unit dosage into a tablet, various biodegradable or biocompatible carriers well known in the art may be widely used. Examples of such carriers include brine-based aqueous solution and various buffer solutions, ethanol or other polyols, liposomes, polylactic acid, vinyl acetate, polyanhydride, polyglycolic acid, collagen, polyorthodester, etc.

The administration dose of the modified peptides according to the present invention depends on many factors, such as the properties and severity of the diseases to be prevented or treated, gender, age, body weight, susceptibility, and individual response of the patients or animal, the concrete compound to be employed, administration routes, administration times, and the desired therapeutic effect. Said dose may be administered in a single dosage unit or in several, such as two, three or four dosage units. A person skilled in the art can determine the concrete dose of the PEG-modified Exendin-4 analogs of the present invention by reference to the known doses of Exendin-4 in combination with the research results from conventional assays, without paying creative work.

Some abbreviates used in the present invention have the following meanings:

Ex-4 represents Exendin-4;
PEG represents polyethylene glycol;
Aa represents amino acid;
Ala represents alanine; Arg represents arginine;
Asn represents asparagine; Asp represents aspartic acid;
Cys represents cysteine; Gln represents glutamine;
Glu represents glutamic acid; Gly represents glycine;
His represents histidine; Hyp represents hydroxyproline;
Ile represents isoleucine; Leu represents leucine;
Lys represents lysine; Met represents methionine;
Phe represents phenylalanine; Pro represents proline;
Ser represents serine; Thr represents threonine;
Thp represents thioproline; Trp represents tryptophan;
Tyr represents tyrosine; Val represents valine;
Fmoc represents fluorenylmethyloxycarbonyl;
DMF represents N,N-dimethylformamide;
DCC represents N,N'-dicyclohexylcarbodiimide;
HOBt represents 1-Hydroxybenzotriazole;
TFA represents trifluoroacetic acid;
EDT represents mercaptoethanol;
HBTU represents 2-(1H-Hydroxybenzotriazole-1-yl)-1,1,3,3-tetramethyluronium hexafluorophosphate;
RP-HPLC represents reverse phase high performance liquid chromatography.

Other un-indicated abbreviations have the meanings recognized in the art.

EXAMPLES

The present invention is further described by the following examples. However, the scope of the present invention is not limited to the following examples. A person skilled in the art would understand that various alteration and modification may be made to the present invention without departing from the spirit and scope of the present invention. The present invention makes general and/or specific depiction on the materials and experimental methods used in the experiments. Although many materials and operations used for achieving the purpose of the present invention are well known in the art, the present invention still describes them as detailed as possible.

The carrier for solid-phase synthesis used in the Examples, i.e. Rink-amide resin, is a product from TIANJIN NANKAI GUARD CO., LTD.; HOBT, HBTU, DIEA and Fmoc-protected natural amino acids are purchased from GL Biochem (Shanghai) Ltd.; the PEG-modified moiety represented by "PEG-M" in Formula (I) (for example, mPEG$_{5000}$-MAL used in the Examples) is a product from Kaizheng Biotech Ltd. Co.

Example 1

Synthesis of [Cys$^{21}$(mPEG5000-MAL)]Exendin-4 (Compound 1)

Step 1: Solid-Phase Synthesis of [Cys$^{21}$]Exendin-4

Based on the amino acid sequence of Compound 1, the peptide resin was synthesized by the standard Fmoc solid-phase peptide synthetic method, wherein 670 mg Rink-amide resin (0.25 mmol) was used as solid-phase carrier; Fmoc-Ala-OH, Fmoc-Arg(pbf)-OH, Fmoc-Asn(Trt)-OH, Fmoc-Asp (OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Trp-OH, Fmoc-Val-OH were used as raw materials; HBTU-HOBt was used as condensing agent. The peptide was de-protected and was cleaved from the resin by using 25 ml of trifluoroacetic acid: thioanisole: metacresol: dithioglycol: water (in a volume ratio of 8.25:0.5:0.5:0.25:0.5) as the cleavage solution and incubating at 0° C. for 30 min and then at room temperature for 90 min. The crude peptide was dissolved in 20% acetic acid aqueous solution, and was lyophilized to give while powder (719 mg). After purification of the crude peptide by RP-HPLC, the bio-mass spectrometry determined that its molecular weight was 4176, and the retention time was 10.365 min. HPLC conditions were as followed: A phase: 0.05% TFA/water, B phase: 0.05% TFA/70% ACN/water, chromatographic column: phenomenex jupiler 5u C4 300 A 4.6×250 mm; gradient: 0-17 min B % 35-85; 17-21 min B % 85-35; finished at 25 min; flow rate: 1 mL/min; column temperature: 25° C.

Step 2: The Reaction of the Polypeptide with PEG-Modified Moiety

[Cys$^{21}$]Exendin-4 purified by RP-HPLC was dissolved in phosphate buffer, an appropriate amount of mPEG$_{5000}$-MAL was added, and the reaction took place at room temperature. RP-HPLC was used to monitor the reaction and isolate the products. The MALDI-TOF-MS result showed that the product had Mn=9135, a molecular weight difference of about 44 between two contiguous peaks, and a typical structural characteristic of polyethylene glycol. The retention time of RP-HPLC was 12.925 min.

Example 2

Synthesis of [Cys$^{22}$(mPEG$_{5000}$-MAL)]Exendin-4 (Compound 2)

Please refer to Example 1 for the synthetic method.
[Cys$^{22}$]Exendin-4 had a molecular weight of 4142, and a retention time of 10.86 min. The MALDI-TOF-MS result showed that the PEG-modified product had Mn=9146, a molecular weight difference of about 44 between two contiguous peaks, and a typical structural characteristic of polyethylene glycol, and RP-HPLC retention time of 10.438 min.

Example 3

Synthesis of [Cys$^{23}$(mPEG$_{5000}$-MAL)]Exendin-4 (Compound 3)

Please refer to Example 1 for the synthetic method.
[Cys$^{23}$]Exendin-4 had a molecular weight of 4176, and a retention time of 10.875 min. The MALDI-TOF-MS result showed that the PEG-modified product had Mn=9180, a molecular weight difference of about 44 between two contiguous peaks, and a typical structural characteristic of polyethylene glycol, and RP-HPLC retention time of 11.52 min.

Example 4

Synthesis of [Cys$^{31}$(mPEG$_{5000}$-MAL)]Exendin-4 (Compound 4)

Please refer to Example 1 for the synthetic method.
[Cys$^{31}$]Exendin-4 had a molecular weight of 4192, and a retention time of 11.15 min. The MALDI-TOF-MS result showed that the PEG-modified product had Mn=9150, a molecular weight difference of about 44 between two contiguous peaks, and a typical structural characteristic of polyethylene glycol, and RP-HPLC retention time of 11.72 min.

Example 5

Synthesis of [Cys$^{36}$(mPEG$_{5000}$-MAL)]Exendin-4 (Compound 5)

Please refer to Example 1 for the synthetic method.
[Cys$^{36}$]Exendin-4 had a molecular weight of 4192, and a retention time of 11.21 min. The MALDI-TOF-MS result showed that the PEG-modified product had Mn=9151, a molecular weight difference of about 44 between two contiguous peaks, and a typical structural characteristic of polyethylene glycol, and RP-HPLC retention time of 11.88 min.

Example 6

Synthesis of [Cys$^{37}$(mPEG$_{5000}$-MAL)]Exendin-4 (Compound 6)

Please refer to Example 1 for the synthetic method.
[Cys$^{37}$]Exendin-4 had a molecular weight of 4192, and a retention time of 10.92 min. The MALDI-TOF-MS result showed that the PEG-modified product had Mn=9150, a molecular weight difference of about 44 between two contiguous peaks, and a typical structural characteristic of polyethylene glycol, and RP-HPLC retention time of 11.82 min.

Example 7

Synthesis of [Cys$^{38}$(mPEG$_{5000}$-MAL)]Exendin-4 (Compound 7)

Please refer to Example 1 for the synthetic method.

[Cys$^{38}$]Exendin-4 had a molecular weight of 4192, and a retention time of 11.24 min. The MALDI-TOF-MS result showed that the PEG-modified product had Mn=9153, a molecular weight difference of about 44 between two contiguous peaks, and a typical structural characteristic of polyethylene glycol, and RP-HPLC retention time of 11.90 min.

Example 8

Synthesis of [Thp$^{31}$(mPEG$_{5000}$-MAL)]Exendin-4 (Compound 8)

Fmoc-Thp(Trt)-OH was used as the raw material for the amino acid Thp. Please refer to Example 1 for the synthetic method.

[Thp$^{31}$]Exendin-4 had a molecular weight of 4218, and a retention time of 11.02 min. The MALDI-TOF-MS result showed that the PEG-modified product had Mn=9221, a molecular weight difference of about 44 between two contiguous peaks, and a typical structural characteristic of polyethylene glycol, and RP-HPLC retention time of 11.45 min.

Example 9

Synthesis of [Thp$^{36}$(mPEG$_{5000}$-MAL)]Exendin-4 (Compound 9)

Please refer to Example 8 for the synthetic method.

[Thp$^{36}$]Exendin-4 had a molecular weight of 4218, and a retention time of 10.95 min. The MALDI-TOF-MS result showed that the PEG-modified product had Mn=9222, a molecular weight difference of about 44 between two contiguous peaks, and a typical structural characteristic of polyethylene glycol, and RP-HPLC retention time of 11.62 min.

Example 10

Synthesis of [Thp$^{37}$(mPEG$_{5000}$-MAL)]Exendin-4 (Compound 10)

Please refer to Example 8 for the synthetic method.

[Thp$^{37}$]Exendin-4 had a molecular weight of 4218, and a retention time of 10.82 min. The MALDI-TOF-MS result showed that the PEG-modified product had Mn=9222, a molecular weight difference of about 44 between two contiguous peaks, and a typical structural characteristic of polyethylene glycol, and RP-HPLC retention time of 11.43 min.

Example 11

Synthesis of [Thp$^{38}$(mPEG$_{5000}$-MAL)]Exendin-4 (Compound 11)

Please refer to Example 8 for the synthetic method.

[Thp$^{38}$]Exendin-4 had a molecular weight of 4218, and a retention time of 10.91 min. The MALDI-TOF-MS result showed that the PEG-modified product had Mn=9221, had a molecular weight difference of about 44 between two contiguous peaks, and had a typical structural characteristic of polyethylene glycol, and RP-HPLC retention time of 11.74 min.

Example 12

Synthesis of [Cys$^{31}$(mPEG$_{20000}$-MAL)]Exendin-4 (Compound 12)

Please refer to Example 1 for the synthetic method. [Cys$^{31}$] Exendin-4 peptide analog was analyzed under the following spectrometic conditions.

[Cys$^{31}$]Exendin-4 peptide analog had a molecular weight of 4192, and a retention time of 8.838 min. The MALDI-TOF-MS result showed that the PEG-modified product had Mn=25682, a molecular weight difference of about 44 between two contiguous peaks, and a typical structural characteristic of polyethylene glycol, and RP-HPLC retention time of 9.70 min. HPLC conditions were as followed: A phase: 0.05% TFA/water; B phase: 0.05% TFA/70% ACN/water; chromatographic column: Agilent zorbax 5u C18 300 A 4.6×150 mm; gradient: 0-15 min B % 35-85; 15-17 min B % 85-35; finished at 20 min; flow rate: 1 mL/min; column temperature: 25° C.

It could be seen from the results of the above synthesis and analyses that the present invention obtained mono-PEG-modified Exendin-4 analogs. Due to the high reactivity of the active hydrosulfuryl in the peptide chain of the Exendin-4 analogs, PEG may be linked to the Exendin-4 analogs in a site-directed manner.

Assay 1

Evaluation of Agonistic Activity on GLP-1 Receptor

GLP-1 receptor is a Gs-coupled GPCR. CRE-luciferase reporter system was stably expressed in human embryonic kidney epithelial cell line HEK293 used for evaluation. Therefore, once the receptor was activated, the enhancement of intracellular concentration of the second messenger cAMP through Gs signal pathway would initiate the expression of the luciferase gene in the reporter system. The ability of the test compounds to stimulate and activate GLP-1 receptor was reflected by the detected expression level of the luciferase reporter gene.

By referring to the methods described in the document (Yin Fei et al., Chinese Pharmaceutical Journal, 2007, 42(1): 24), the GLP-1 receptor agonistic activity of the PEG-modified Exendin-4 analogs was determined in cellular level. Exendin-4 had an EC$_{50}$ of 1.93 nM. The results were shown in Table 1.

TABLE 1

The GLP-1 receptor agonistic activity of the PEG-modified Exendin-4 analogs.

| Compound No. | Sequence | EC$_{50}$ (nM) |
| --- | --- | --- |
| 1 | [Cys$^{21}$(mPEG$_{5000}$-MAL)] Exendin-4 | 22.46 |
| 2 | [Cys$^{22}$(mPEG$_{5000}$-MAL)] Exendin-4 | 19.75 |
| 3 | [Cys$^{23}$(mPEG$_{5000}$-MAL)] Exendin-4 | 15.77 |
| 4 | [Cys$^{31}$(mPEG$_{5000}$-MAL)] Exendin-4 | 0.58 |
| 5 | [Cys$^{36}$(mPEG$_{5000}$-MAL)] Exendin-4 | 1.53 |
| 6 | [Cys$^{37}$(mPEG$_{5000}$-MAL)] Exendin-4 | 1.76 |

TABLE 1-continued

The GLP-1 receptor agonistic activity of the PEG-modified Exendin-4 analogs.

| Compound No. | Sequence | $EC_{50}$ (nM) |
| --- | --- | --- |
| 7 | [$Cys^{38}$($mPEG_{5000}$-MAL)] Exendin-4 | 10.72 |
| 8 | [$Thp^{31}$($mPEG_{5000}$-MAL)] Exendin-4 | 6.36 |
| 9 | [$Thp^{36}$($mPEG_{5000}$-MAL)] Exendin-4 | 7.46 |
| 10 | [$Thp^{37}$($mPEG_{5000}$-MAL)] Exendin-4 | 8.01 |
| 11 | [$Thp^{38}$($mPEG_{5000}$-MAL)] Exendin-4 | 28.19 |
| 12 | [$Cys^{31}$($mPEG_{20000}$-MAL)] Exendin-4 | 1.84 |

It could be seen from Table 1 that all the PEG-modified Exendin-4 analogs of the present invention had an effective GLP-1 agonistic activity.

The invention claimed is:

1. A PEG-modified Exendin-4 analog as shown in Formula (I)

$$PEG-M-X-(Ex-4) \quad (I),$$

or a pharmaceutically acceptable salt thereof, wherein
PEG represents $RO(CH_2CH_2O)_n-CH_2CH_2-$, wherein R is H or $CH_3$, and n is an integer of 25-2500;
M represents

[chemical structures shown]

and is linked to a PEG moiety by the nitrogen or sulfur atom of each of them on one side and is linked to the hydrosulfuryl of X moiety on the other side;

X-(Ex-4) represents an Exendin-4 analog having the following structure: His-Gly-Glu-Gly-Thr-Phe-Thr-Ser-Asp-Leu-Ser-Lys-Gln-Met-Glu-Glu-Glu-Ala-Val-Arg-$Aa_{21}$-$Aa_{22}$-$Aa_{23}$-Glu-Trp-Leu-$Aa_{27}$-Asn-Gly-Gly-$Aa_{31}$-Ser-Ser-Gly-Ala-$Aa_{36}$-$Aa_{37}$-$Aa_{38}$-Ser-$NH_2$(SEQ ID NO: 2), wherein, the $Aa_{21}$ is selected from the group consisting of Cys, Thp and Leu;

the $Aa_{22}$ is selected from the group consisting of Cys, Thp and Phe;

the $Aa_{23}$ is selected from the group consisting of Cys, Thp and Ile;

the $Aa_{27}$ is selected from the group consisting of Cys, Thp and Lys;

the $Aa_{31}$ is selected from the group consisting of Cys, Thp and Pro;

the $Aa_{36}$ is selected from the group consisting of Cys, Thp and Pro;

the $Aa_{37}$ is selected from the group consisting of Cys, Thp and Pro;

and the $Aa_{38}$ is selected from the group consisting of Cys, Thp and Pro;

provided that only one of $Aa_{21}$, $Aa_{22}$, $Aa_{23}$, $Aa_{27}$, $Aa_{31}$, $Aa_{36}$, $Aa_{37}$ and $Aa_{38}$ is Cys or Thp;

X represents an amino acid at position 21, 22, 23, 27, 31, 36, 37 or 38 that is cysteine or 4-thioproline (Thp,

[chemical structure shown]

)

in the Exendin-4 analog as shown in X-(Ex-4), wherein the hydrosulfuryl of the amino acid is linked to the M group.

2. The PEG-modified Exendin-4 analog according to claim 1 or a pharmaceutically acceptable salt thereof, wherein PEG represents polyethylene glycol with a molecular weight of 1,000-100,000.

3. The PEG-modified Exendin-4 analog according to claim 1 or a pharmaceutically acceptable salt thereof, wherein n is an integer of 50-2000, an integer of 50-1500, an integer of 50-1000, an integer of 75-1500, an integer of 75-1000, an integer of 75-500, or an integer of 100-500.

4. The PEG-modified Exendin-4 analog according to claim 1 or a pharmaceutically acceptable salt thereof, wherein the PEG represents polyethylene glycol with a molecular weight of 1,000-100,000, 2,000-80,000, 3,000-60,000, 4,000-60,000, 5,000-60,000, 3,000-50,000, 4,000-40,000, 4,000-30,000, or 5,000-20,000.

5. The PEG-modified Exendin-4 analog according to claim 1 or a pharmaceutically acceptable salt thereof, wherein X represents an amino acid at position 21, 22, 23, 31, 36, 37 or 38 that is cysteine or 4-thioprolinein the Exendin-4 analogs as shown in X-(Ex-4).

6. The PEG-modified Exendin-4 analog according to claim 5 or a pharmaceutically acceptable salt thereof, wherein X represents an amino acid at position 21, 22, 23, 31, 36, 37 or 38 that is cysteine in the Exendin-4 analogs as shown in X-(Ex-4).

7. The PEG-modified Exendin-4 analog according to claim 5 or a pharmaceutically acceptable salt thereof, wherein X represents an amino acid at position 31, 36, 37 or 38 that is 4-thioprolinein the Exendin-4 analogs as shown in X-(Ex-4).

8. The PEG-modified Exendin-4 analog according to claim 1, which is a site-directed, PEG-modified Exendin-4 analog, or a pharmaceutically acceptable salt thereof.

9. The PEG-modified Exendin-4 analog according to claim 1, which is a site-directed PEG-modified Exendin-4 analog, or a pharmaceutically acceptable salt thereof, wherein the PEG-modification is a mono-PEG-modification.

10. The PEG-modified Exendin-4 analog according to claim 1, which is selected from the group consisting of

[$Cys^{21}$($mPEG_{5000}$-MAL)] Exendin-4,
[$Cys^{22}$($mPEG_{5000}$-MAL)] Exendin-4,
[$Cys^{23}$($mPEG_{5000}$-MAL)] Exendin-4,
[$Cys^{31}$($mPEG_{5000}$-MAL)] Exendin-4,
[$Cys^{36}$($mPEG_{5000}$-MAL)] Exendin-4,
[$Cys^{37}$($mPEG_{5000}$-MAL)] Exendin-4,
[$Cys^{38}$($mPEG_{5000}$-MAL)] Exendin-4,
[$Thp^{31}$($mPEG_{5000}$-MAL)] Exendin-4,
[$Thp^{36}$($mPEG_{5000}$-MAL)] Exendin-4,
[$Thp^{37}$($mPEG_{5000}$-MAL)] Exendin-4,
[$Thp^{38}$($mPEG_{5000}$-MAL)] Exendin-4, and
[$Cys^{31}$($mPEG_{20000}$-MAL)] Exendin-4, or a pharmaceutically acceptable salt thereof.

11. An Exendin-4 analog as shown in Formula (II)

$$[Aa^p] \text{ Exendin-4} \quad (II),$$

or a pharmaceutically acceptable salt thereof, wherein

Exendin-4 represents 39-amino acid peptide of His-Gly-Glu-Gly-Thr-Phe-Thr-Ser-Asp-Leu-Ser-Lys-Gln-Met-Glu-Glu-Glu-Ala-Val-Arg-$Aa_{21}$-$Aa_{22}$-$Aa_{23}$-Glu-Trp-Leu-$Aa_{27}$-Asn-Gly-Gly-$Aa_{31}$-Ser-Ser-Gly-Ala-$Aa_{36}$-$Aa_{37}$-$Aa_{38}$-Ser-$NH_2$ (SEQ ID NO: 2), wherein $Aa_{21}$ is Leu, $Aa_{22}$ is Phe, $Aa_{23}$ is Ile, $Aa_{27}$ is Lys, $Aa_{31}$ is Pro, $Aa_{36}$ is Pro, $Aa_{37}$ is Pro, and $Aa_{38}$ is Pro;

$Aa^p$ represents an amino acid for further substituting an amino acid at position p of the 39-amino acid peptide as shown in Exendin-4, which is cysteine (Cys) or 4-thioproline (Thp or

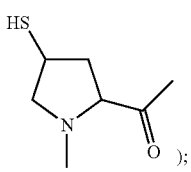

p represents position 21, 22, 23, 27, 31, 36, 37 or 38 of the 39-amino acid peptide as shown in Exendin-4.

12. The Exendin-4 analog according to claim 11 or a pharmaceutically acceptable salt thereof, wherein
Aa$^p$ represents cysteine for substituting the amino acid at position p of the 39-amino acid peptide as shown in Exendin-4,
p represents position 21, 22, 23, 31, 36, 37 or 38 of the 39-amino acid peptide as shown in Exendin-4.

13. The Exendin-4 analog according to claim 11 or a pharmaceutically acceptable salt thereof, wherein
Aa$^p$ represents 4-thioproline for substituting the amino acid at position p of the 39-amino acid peptide shown in Exendin-4; and
p represents position 31, 36, 37 or 38 of the 39-amino acid peptide as shown in Exendin-4.

14. The Exendin-4 analog according to claim 11, which is selected from the group consisting of
1 [Cys$^{21}$] Exendin-4,
2 [Cys$^{22}$] Exendin-4,
3 [Cys$^{23}$] Exendin-4,
4 [Cys$^{31}$] Exendin-4,
5 [Cys$^{36}$] Exendin-4,
6 [Cys$^{37}$] Exendin-4,
7 [Cys$^{38}$] Exendin-4,
8 [Thp$^{31}$] Exendin-4,
9 [Thp$^{36}$] Exendin-4,
10 [Thp$^{37}$] Exendin-4, and
11 [Thp$^{38}$] Exendin-4,
or a pharmaceutically acceptable salt thereof.

15. A method for treatment of diseases and/or symptoms associated with low activity of GLP-1 receptors in a subject by activation of the GLP-1 receptors in the subject in need thereof, the method comprising administering a therapeutically effective amount of a PEG-modified Exendin-4 analog according to claim 1 or a pharmaceutically acceptable salt thereof, wherein the treatment of diseases and/or symptoms include:
treatment of diseases and/or symptoms associated with low activity of GLP-1 receptor;
control of glyceride, promotion of insulin secretion, reduction of circulating glucagons, enhancement of pancreatic β-cell quality, inhibition of gastric emptying, reduction of intake of nutrition, and increase in sensitivity to insulin;
treatment of diseases and/or symptoms associated with glucose metabolism;
treatment of glucose metabolism diseases such as Type II diabetes, obesity and/or adiposity, and hypofunction of β cells; and/or
glycemic control in a patient suffering from type II diabetes.

* * * * *